United States Patent [19]

Moss

[11] Patent Number: 5,133,362
[45] Date of Patent: Jul. 28, 1992

[54] NEEDLE FOR USE WITH VACUUM TEST TUBE BLOOD SAMPLING SYSTEMS

[76] Inventor: Gerald Moss, RD #1, West Sand Lake, N.Y. 12196

[21] Appl. No.: 635,774

[22] Filed: Dec. 28, 1990

[51] Int. Cl.⁵ .............................................. A61B 5/00
[52] U.S. Cl. ................................... 128/763; 604/264
[58] Field of Search .................. 128/760, 763, 770; 640/264, 272

[56] References Cited

U.S. PATENT DOCUMENTS

| | | |
|---|---|---|
| 2,193,322 | 3/1940 | Lozier et al. |
| 2,847,994 | 8/1958 | Huber |
| 3,368,557 | 2/1968 | Hassings et al. |
| 3,382,865 | 5/1968 | Woenall |
| 3,768,474 | 10/1973 | Burke et al. |
| 3,817,240 | 6/1974 | Ayers |
| 3,884,229 | 5/1975 | Raines et al. |
| 3,931,815 | 1/1976 | Takatsuki |
| 4,266,543 | 5/1981 | Blum .................. 128/763 |
| 4,326,541 | 4/1986 | Eckels ................ 128/766 |
| 4,340,068 | 7/1982 | Kaufman ............ 128/766 |
| 4,713,062 | 12/1987 | Stevanato ........... 604/203 |
| 4,844,089 | 7/1989 | Roberti ............... 128/764 |

FOREIGN PATENT DOCUMENTS 2081231  2/1982  United Kingdom.

*Primary Examiner*—Max Hindenburg
*Attorney, Agent, or Firm*—Schmeiser, Morelle & Watts

[57] ABSTRACT

In a double needle the blood withdrawal system the front needle for accomplishing the vena puncture is between 23 gauge and 29 gauge while the rear needle which resides in the syringe barrel and is used to puncture the stopper is similar to those standardly used between 12 and 16 gauge. The smaller gauge front needle acts as a flow restricter to prevent the initial blood sample drawn into the vacuum tube from impacting on the bottom wall of the tube thereby creating hemolysis of some of the red cells. The length of the front needle is between 0.5 and 1.5 inches.

3 Claims, 2 Drawing Sheets

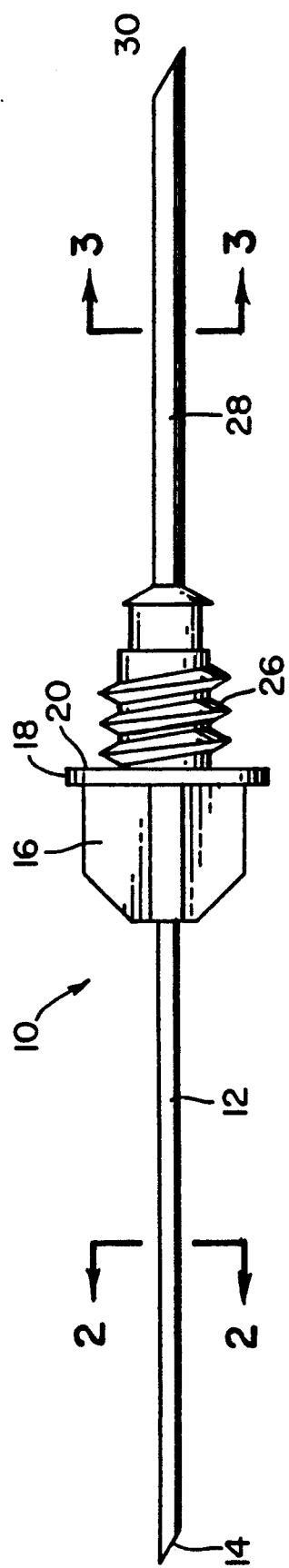
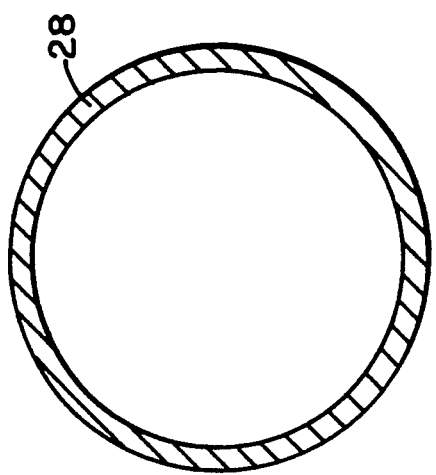
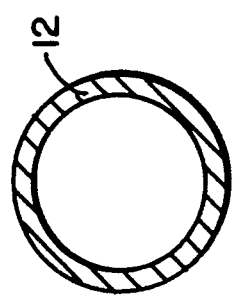
FIG. 1
FIG. 3
FIG. 2

NEEDLE FOR USE WITH VACUUM TEST TUBE BLOOD SAMPLING SYSTEMS

FIELD OF THE INVENTION

Generally, this invention relates to needles used in the medical field for the withdrawal of liquids from the body. More specifically, this invention is an improvement in blood sampling systems which utilize double needles wherein a front needle is utilized for the vena puncture and a rear needle is used to puncture the rubber stopper of a vacuum test tube.

BACKGROUND OF THE INVENTION

The use of double needles for the withdrawal of blood is widely known and accepted. Such needles may be manufactured to be integrally formed with a syringe barrel or they may be manufactured separately with external threading so that the double needle may be secured into the end of an appropriate syringe barrel. A typical double needle of the latter type is marketed under the trademark VACUTAINER which is owned by the Becton Dickenson Corporation.

With both the integral unit and the separate double needle, both needle configurations are the same. Namely, one needle extends upward centrally into the syringe barrel while the other needle extends in the opposite direction, outwardly from the syringe barrel. The latter needle is used to accomplish the vena puncture.

In the manufacture of these needles the only concern for the gauge of the needle is that the needle which extends into the syringe barrel must be sufficiently rigid to puncture the rubber test tube stopper without the needle bending or buckling. The needle which is used to accomplish the vena puncture has previously no been a concern and it is typically of a standard blood withdrawal size which is between 12 and 16 gauge. These gauge sizes are of the type typically used for blood donors, who by law must be of at least a certain age and are generally not frail or infirm. The automatic transfer of these needle sizes from such a use to a use on patients who may be young or may be frail, fails to recognize a major disadvantage of the double needle vacuum tube blood withdrawal systems presently in use. Some double needle systems are scaled down for use with small syringe barrels where only a small sample of blood is required. In these scaled down systems the needles may be approximately 21 gauge.

The gauge of the needle refers to standard wire gauge measurements and defines the outer diameter of the needle. The inner opening of the needle is generally not defined but relates directly to the gauge and the use of either a thin wall or standard wall needle which are well known in the medical field. For the purposes of this application the commonly used gauges will be utilized. It should also be appreciated that either a thin wall or standard wall may be used without significantly effecting the actual opening of the needle and the flow rates of the blood passing therethrough.

In use, one or more vacuum test tubes are placed in proximity to the patient and may in fact, be placed within the syringe barrel with the stopper of the test tube near or against the tip of the second (rear) needle, but without the rear needle piercing the stopper or disrupting the vacuum seal. The first (front) needle is then used to accomplish the vena puncture which would result in some blood traveling through the needle toward the syringe barrel at a relatively slow rate, as determined by the pressure within the patient's vein. Once the vena puncture is accomplished, the test tube is advanced into the syringe barrel until the second needle pierces the test tube and the vacuum in the test tube quickly draws the blood through the needle and into the test tube. It is common that during this initial puncture the blood will initially squirt into the test tube and against the test tube wall. As the pressure within the test tube and that within the vein seek equilibrium blood fills the tube which blood acts as a cushion for the new blood entering the tube.

For these systems to work properly the test tubes must have a sufficient vacuum to draw enough blood into the test tube for future testing. To accomplish this and due to difficulties that exist should a test tube be used which does not have sufficient vacuum pressure, the tendency is to create more of a vacuum within the tubes than is actually needed. The purpose of this being to avoid the situation where additional vacuum tubes have to be used to obtain a sufficient amount of blood to accomplish the desired testing. Also, one of the main purposes of this system is to reduce the direct handling of the blood and thus, separate test tubes are generally used for separate tests and if a particular test tube does not withdraw enough blood to accomplish that test then that test tube and the blood is simply discarded and a complete new test tube for the desired testing is utilized. One can appreciate the type of frustration and difficulties that would result if a tube or several tubes in a row did not have a sufficient vacuum to withdraw the necessary amount of blood for testing.

The results of this manufacturing process, which seeks to make the test tubes with a significant vacuum, is that when used, there is an initial pulse of blood as maximum suction is applied at the first piercing of the stopper. With the use of these relatively large gauge needles (12-16 gauge) this initial pulse actually squirts the blood into the test tube. When this initial blood impacts in the test tube there is a measurable amount of hemolysis. Whenever hemolysis is created in the blood sample there is a skewing of the test results because there are now less red cells due to their hemolysis and the contents of the now hemolysized red cell are floating freely within the sample.

When the patient has veins which are relatively healthy and resilient there is no difficulty in the vein absorbing a number of vena punctures from these large needles with no adverse effect. However, where the patient is an infant or if the resiliency of the vein has been diminished due to age or illness, numerous vena punctures can cause vein blockages which has a detrimental effect on the treatment as additional veins must be located and used in order to maintain the necessary monitoring. This problem is further exacerbated in those situations where blood needs to be drawn frequently to monitor the patient's progress or condition. In these latter situations it is not uncommon for the patient to virtually exhaust their supply of suitable veins for the withdrawal of blood. In fact, it is not uncommon that a person with fragile veins and requiring numerous blood withdrawals and/or transfusions may have only one or two veins that are suitable for the easy withdrawal of blood. In these situations, the blockage of a vein may require surgical procedures in order to obtain access to a vein for obtaining blood samples.

It should be noted that it is common for the prior art to disclose in the drawings, a possible size variation between the rear needle and the front needle. This occurs because in some situations the rear needle which punctures the stopper is of a gauge which is too large for a vena puncture on even a healthy person. Thus, while some size variation may be disclosed in the drawings there is no disclosure of the problem addressed by the subject invention and no disclosure of the parameters necessary to achieve the solution to that problem.

By transferring the same size vena puncture needles used when healthy people donate blood to hospital usages where the patient has fragile veins disregards the physician needs to obtain as accurate blood data as possible and to care for the blood source and seek to obtain vein longevity. It was with these ideas in mind that I sought to maintain the present system which has the advantages of limiting blood contact while reducing the negative effects of the present system to an acceptable level. The subject invention is the result of these efforts.

SUMMARY OF THE INVENTION

The subject invention utilizes a double needle system wherein the second or rear needle is of a gauge similar to those presently being used, namely, 12 to 16 gauge and is also of similar length for successful piercing of the test tube stopper. However, the first or front needle which is used for the vena puncture is reduced in size to be no larger than 23 gauge and preferably 25 gauge or smaller. The length of the front needle is between 0.5 and 1.5 inches. Thus, the first or front needle serves as a restricting conduit which slows the withdrawal of blood and thereby reduces the flow rate through the double needle. Thus, as the blood flows from the smaller front needle into the larger rear needle the flow rate reduction prevents the blood from impacting against the back wall of the test tube and generally slows the flow of blood into the tube. Thus, by limiting the length of the front needle and also limiting its gauge while maintaining the gauge of the second or rear needle, a much improved system of blood withdrawal is obtained.

While the recognition of the problem as set forth above, was a significant step in the development of the solution embodied in the subject invention it was also necessary to draw upon research which I performed regarding the presumed hemolysis of red blood cells when passing through a small conduit. Prior to these double needle systems it was common to withdraw blood for testing with a standard syringe and needle. Often it was the case that a small needle was used both for the vena puncture and to expel the blood from the syringe into a test tube or other depository for testing. A general concern of the medical profession, which I proved was not founded, was that the transfer of red blood cells through a small conduit will create a break down of the red cells commonly referred to as hemolysis. When hemolysis occurs the testing for various blood ingredients such as red cells and the like become skewed. Because of my studies in this area and my test results that there is no significant hemolysis so long as the needle size is no smaller than 29 gauge, I realized that I could use a restricting first needle conduit to overcome the hemolysis problem of the prior art without creating new difficulties.

In addition, the use of this restrictive conduit has another evident benefit in that the smaller needle will create less trauma at the puncture site.

Therefore, restricting the blood flow rate sufficiently by means of the first needle will prevent hemolysis that could skew the sample results, so long as the gauge of the first needle is within certain perameters and the standard vacuum tubes are used.

A full appreciation of this invention may be obtained through a study of the disclosure and practice with the invention.

BRIEF DESCRIPTION OF THE DRAWINGS

FIG. 1 is an enlarged side elevational view of the invention;

FIG. 2 is a view taken along lines 2—2 of FIG. 1;

FIG. 3 is a view taken along lines 3—3 of FIG. 1; and

DETAILED DESCRIPTION OF THE PREFERRED EMBODIMENT

Figure 4:
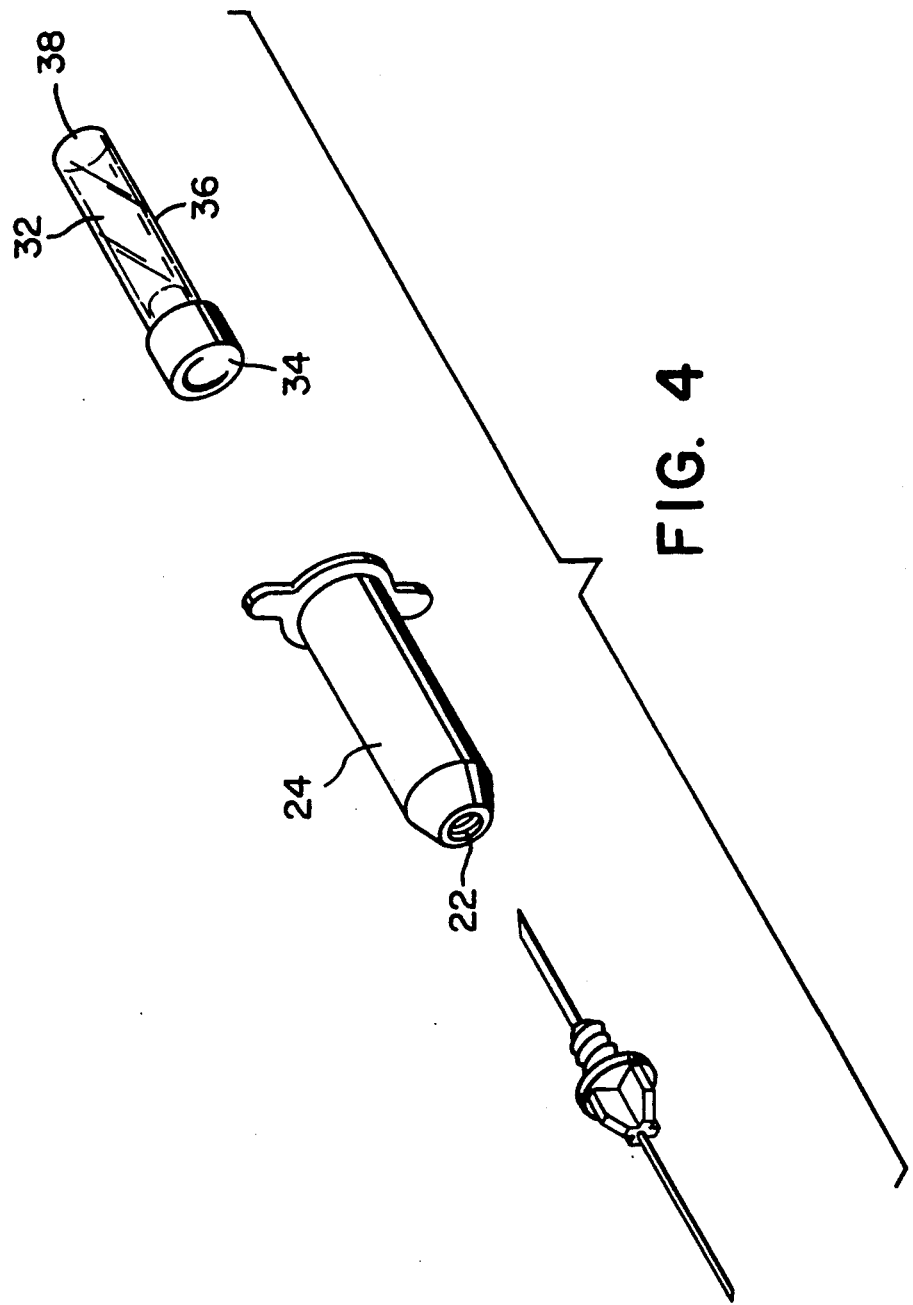
FIG. 4 is perspective view of the invention incorporated into a typical blood withdrawal system.

As shown in FIG. 1 the subject invention is a double needle 10. The double needle has a first or front needle 12, for accomplishing the vena puncture, which is between 23 and 29 gauge and between 0.5 and 1.5 inches long. Preferable, the best results are achieved when the needle is from 25 to 27 gauge. The front needle has a bevel 14 at its distal end and is secured into a base 16 at its proximal end. A base plate 18 is formed at the center point of the double needle. In use, as shown in FIG. 4, the rear face 20 of the base plate is secured against the inlet walls 22 of the syringe barrel 24. Back from the base plate 18 is an externally threaded insert 26 and extending outwardly from the insert 26 is the second or rear needle 28 the end of which also has a bevel 30.

FIGS. 2 and 3 show the approximate relationship of the needles wherein the rear needle 28 is shown in FIG. 3. In the preferred embodiment the rear needle would be about 14 gauge and the front needle 12 as shown in FIG. 2 has a smaller gauge which needs to be between 23 and 29 gauge. It should be appreciated that the figure in the drawings have been enlarged in order to provide a better appreciation for the comparative sizes and the manner in which the double needle functions.

As shown in FIG. 4, the double needle 10 is inserted into the syringe barrel 24 with the externally threaded insert 26 being screwed into the internally threaded inlet 22. Once the vena puncture is accomplished, the test tube 32 is slid down the syringe barrel until the stopper 34 is punctured by the rear needle 28. Since the test tube is vacuum packed the blood will be drawn through the system and into the vacuum test tube. However, the front needle will restrict the blood flow rate sufficiently that when the blood enters the test tube through the rear needle the blood will flow gently onto the sides 36 of the tube and not impact against the bottom test tube wall 38. This will prevent hemolysis and lead to more accurate test results.

It should be appreciated that while the subject application discloses separating the needle and syringe barrel, they may be combined such that the double needle and the syringe barrel may be produced as a unitary piece. Similarly, other changes may be made without diverging from the teachings of the subject invention which are intended to be limited only by the appended claims.

I claim:

1. A double needle of the type commonly used for the withdrawal of blood samples from patient's comprising:
   a central base member;
   a front flow restricted needle adapted for insertion into the patient and extending outwardly from a side of said base member;
   a rear needle adapted to be inserted into a vacuum test tube, said rear needle extending outwardly from a side of the base member which is opposite said front needle, said front and rear needles being substantially coaxial, the length of said front needle being between ½ and 1½ inches, and the gauge of said front needle being between 23 gauge and 29 gauge.

2. The invention of claim 1 wherein the gauge of said front needle is between 25 gauge and 27 gauge.

3. The invention of claim 2 wherein said front needle is of a standard wall thickness.

* * * * *